United States Patent [19]

Möller et al.

[11] Patent Number: 4,463,006

[45] Date of Patent: Jul. 31, 1984

[54] DIGLYCIDYL-PTERIDINE COMPOUNDS

[75] Inventors: Hinrich Möller, Monheim; Brigitte Hase, Erkrath; Günther Konrad, Hilden; Hans-Christoph Wilk, Neuss; Ulrich Zeidler, Düsseldorf, all of Fed. Rep. of Germany

[73] Assignee: Henkel Kommanditgesellschaft auf Aktien, Duesseldorf, Fed. Rep. of Germany

[21] Appl. No.: 391,174

[22] Filed: Jun. 23, 1982

[30] Foreign Application Priority Data

Aug. 7, 1981 [DE] Fed. Rep. of Germany ....... 3131396

[51] Int. Cl.³ ................. A61K 31/505; C07D 475/02; C07D 475/14
[52] U.S. Cl. .................................. 424/251; 424/252; 544/251; 544/257
[58] Field of Search ............... 544/251, 257; 424/251, 424/252

[56] References Cited

U.S. PATENT DOCUMENTS 4,376,120  3/1983  Zeidler et al. ................... 424/249

FOREIGN PATENT DOCUMENTS 0033503  8/1981  European Pat. Off. ............ 544/251
2907349  8/1980  Fed. Rep. of Germany ...... 424/252

*Primary Examiner*—Paul M. Coughlan, Jr.
*Attorney, Agent, or Firm*—Ernest G. Szoke; Henry E. Millson, Jr.

[57] ABSTRACT

Diglycidyl-substituted pteridine compounds of the general formula:

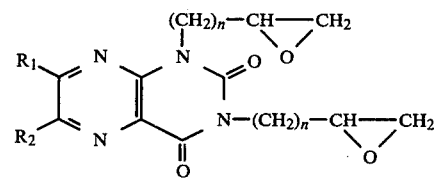

wherein n is the whole number 1 or 2, $R_1$ and $R_2$ are the same or different, and are either hydrogen, a hydrocarbon radical, or together form a 5- or 6-membered carbocyclic or heterocyclic ring; processes for their preparation; and compositions and methods for their use as cytostatic agents.

36 Claims, No Drawings

DIGLYCIDYL-PTERIDINE COMPOUNDS

BACKGROUND OF THE INVENTION

German Patent DE-OS No. 29 07 349 relates to the manufacture of pharmaceutical compositions with cytostatic properties, and which contain as the pharmacologically active ingredient triglycidylisocyanurate (TGI). European Pat. No. 0 033 503 discloses compounds useful in the manufacture of pharmaceutical compositions having cytostatic properties. Such compositions contain N-heterocyclic compounds having at least 2 glycidyl substituted ring nitrogen atoms in amide and/or imide form. In fact, this European patent discloses a multitude of special classes of compounds of the above mentioned type, all of which can be used for the manufacture of pharmaceutical compounds that exhibit tumor inhibiting properties.

DESCRIPTION OF THE INVENTION

The present invention relates to diglycidyl substituted pteridine compounds, having the general Formula I given below:

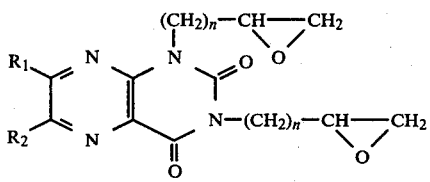

wherein n is the whole number 1 or 2, preferably 1, and $R_1$ and $R_2$ are the same or different, and are either hydrogen, a hydrocarbon radical having not more than 12 carbon atoms, or $R_1$ and $R_2$ together form a 5- or 6-membered carboxylic or heterocyclic ring. Where the term "hydrocarbon radical" is used herein, it is understood to include radicals containing one or more heteroatoms, e.g. O, S, and P. Preferably, the hydrocarbon radical contains no more than 8 carbon atoms, more preferably no more than 6, and most preferably no more than 4 carbon atoms. The hydrocarbon radicals can be chosen from the following:

(a) a straight or branched chain alkyl group, and such group is preferred in the practice of the invention, e.g. methyl, ethyl, propyl, butyl, pentyl, hexyl, octyl, decyl, dodecyl, isopropyl, isobutyl, tert. butyl, isopentyl, 2-methylhexyl, 3-ethyloctyl, etc. The alkyl group may also contain from 1 to 3 oxygen or sulfur atoms, e.g. the alkyl group may contain one of the following moieties: —$CH_2$—$CH_2$—O—$CH_2$—$CH_2$—, or —$CH_2$—$CH_2$—O—$CH_2$—$CH_2$—O—$CH_2$—$CH_2$—, etc.

(b) a straight or branched chain unsaturated hydrocarbon radical, such as alkenyl or alkynyl, preferably an alkenyl radical, e.g. vinyl, allyl, 1-butenyl, 2-butenyl, 2-methylallyl, 2-pentenyl, 1-octenyl, etc. The term "alkenyl" means an unsaturated aliphatic hydrocarbon which contains one or more double bonds and which may be straight or branched chain. The term "alkynyl" means an unsaturated aliphatic hydrocarbon containing one or more triple bonds, e.g. propargyl, butynyl, pentynyl, etc.

(c) a cycloaliphatic hydrocarbon group, preferably a 5- or 6-membered monocyclic group, e.g., cyclopentyl, cyclyhexyl, etc.

(d) an aromatic hydrocarbon-substituted allyl group, e.g. a phenylalkyl group wherein the alkyl group is a $C_1$-$C_6$ straight or branched chain alkyl group, such as benzyl, phenylethyl, 2-phenylisopropyl, 4-ethylbenzyl, 1-naphthylmethyl, etc.

(e) an aromatic hydrocarbon group, e.g. phenyl, naphthyl, tolyl, xylyl, trimethylphenyl, isopropylphenyl, etc.

(f) a heterocyclic group, preferably having a 5- or 6-membered ring, containing at least one of the following heteroatoms-O, N, P, or S, e.g. pyridyl, 2-pyridyl or 3-pyridyl; pyrimidyl, pyrazolyl, imidazolyl, furyl, thienyl, oxazolyl, thiazolyl, piperidino, morpholino, thiomorpholino, etc. It should be noted that when the heteroatom is nitrogen, a hydrogen atom must not be present on the nitrogen atom, since an >N-H group will react with one of the glycidyl groups present in the compounds of Formula I.

(g) a cycloaliphatic hydrocarbon-substituted alkyl group, wherein the cycloaliphatic hydrocarbon moiety is preferably a 5- or 6-membered ring, and the alkyl group is a straight or branched chain alkyl group, e.g. cyclopentylmethyl, cyclohexylethyl, 2-cyclohexylisopropyl, etc.

(h) a heterocyclic-substituted alkyl group, wherein the heterocyclic moiety is as defined in (f) above, and the alkyl group is a straight or branched chain alkyl group, e.g. pyridylmethyl, pyridylethyl, 2-(2-pyridyl)isopropyl, oxazolylbutyl, 2-thienylmethyl, 2-furylmethyl, etc.

When $R_1$ and/or $R_2$ contains an aromatic, cycloaliphatic, or heterocyclic moiety, such moiety is preferably monocyclic. When $R_1$ and $R_2$ together form a 5- or 6-membered heterocyclic ring, the heterocyclic ring preferably has 1, 2, or 3 heteroatoms, and preferably the heteroatoms N, O, S and/or P. Here also, however, an >N-H group must not be present in the heterocyclic ring. When $R_1$ and/or $R_2$ are other than hydrogen, i.e., are a hydrocarbon radical or together form a 5- or 6-membered carbocyclic or heterocyclic ring, substituents may be present thereon. Preferably, from 1 to 3 substituents may be present. Such substituents can be straight or branched chain alkyl, alkenyl, or alkynyl radicals, preferably containing from 1 to 4 carbon atoms, such as methyl, ethyl, propyl, butyl, isopropyl, isobutyl, allyl, 2-methylallyl, propargyl, butynyl, etc; halogen, e.g. fluorine, chlorine, bromine or iodine; alkoxy, preferably having from 1 to 4 carbon atoms; cyano; alkylmercapto; arylmercapto, e.g. phenylmercapto; alkylsulfoxy, e.g. methylsulfoxy; arylsulfoxy, e.g. phenylsulfoxy; aryloxy, e.g. phenyloxy; acyloxy, e.g. $C_1$-$C_6$ acyloxy, such as acetyloxy; etc.

In a preferred version of the compounds of Formula I, $R_1$ and $R_2$ together do not have more than 12 carbon atoms, preferably not more than 10, more preferably not more than 6, and most preferably not more than 4 carbon atoms. It should be noted that when limitations on the number of carbon atoms are given herein for the R group or groups, such limitations are meant to include the total number of carbon atoms in the R group or groups, i.e. including the carbon atoms in any substituents thereon.

The mechanism by which the compounds of Formula I produce cytostatic effects in mammals is not fully understood. Probably, the two glycidyl groups contribute at least in part to this activity. It is also possible that the $R_1$ and $R_2$ groups affect the distribution of lipophilic and hydrophilic preferences in the body, thereby enhancing the absorption of the compounds by the organism.

Compounds of Formula I can be made by either of the following two processes, both starting with a pteridine compound of the general Formula II below, which is unsubstituted in the 1 and 3 positions. Compounds of Formula II and processes for their preparation are known from the literature and accordingly the starting materials of this invention can be prepared by those skilled in the art utilizing such known methods.

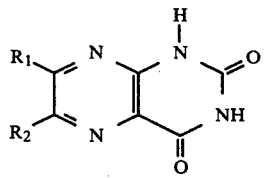

wherein $R_1$ and $R_2$ have the same meanings as in Formula I above,

Examples of compounds of Formula II that can be used in the practice of the invention include lumazine, alloxazine, lumichrome, 6,7-dimethyl-lumazine, 6- or 7-phenyl-alloxazine, and 6,7-diphenyl-lumazine.

Process (A). The compound of Formula II is reacted with an epihalohydrin, such as epichlorohydrin or epibromohydrin, or with a compound of the formula

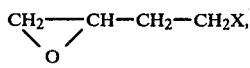

where X is halogen, e.g. chlorine or bromine. The reaction can take place in the presence of a small quantity of a basic catalyst, such as a tertiary amine or a quaternary ammonium compound, see, e.g. Houben-Weyl, "Methoden der organischen Chemie", Vol. 14/2 (1963), 497–547. In this process, both glycidyl groups in the compounds of Formula I are introduced at the same time.

Process (B). The compound of Formula II is reacted with an allyl halide, such as allyl chloride or allyl bromide, or with a 4-halo-1-butene, e.g. 4-chloro-1-butene or 4-bromo-1-butene, to form a substituted compound of Formula III below:

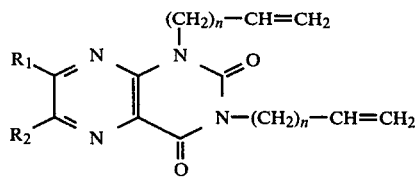

wherein $R_1$, $R_2$ and n have the meaning set forth in Formula I.

The compound of Formula III is then reacted with a peracid to form a compound of Formula I.

The reaction of an allyl halide with cyanuric acid is described in U.S. Pat. No. 3,376,301. The epoxidation of allyl isocyanurates with peracids is described in Houben-Weyl, supra, Vol. 6/3, 385 et seq. The epoxidation step can be carried out in the presence of a small quantity of a quaternary ammonium compound as a catalyst. The same general methods set forth in the above references can be used for the two step process in Process (B).

The reaction of the heterocyclic compounds of Formula II with epihalohydrin or a compound of the formula

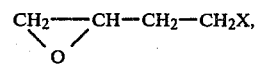

or with an allylhalide or a 1-butenyl halide is normally carried out at a temperature in the range of about 50° to about 150° C., preferably about 60° to about 110° C. The allyl or 1-butenyl halide, or the epihalohydrin or compound of the formula

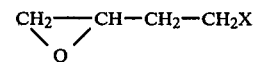

is added in at least the required molar amount; however, excess amounts, for instance up to a molar ratio of about 30:1, can also be used.

A molar ratio in the range from about 5 to about 15 moles of the above halide reactant per mole of the compound of Formula II is particularly useful. The reaction can take place in a polar, aprotic solvent, which partially dissolves at least one of the reactants, and which does not react with the reactants. The reaction can also take place in the absence of a solvent. The preferred reaction time is from about 1 to about 10 hours, preferably about 2 to about 5 hours.

The epoxydation of the allyl or allylmethyl groupings in compounds of Formula III with a peracid is also preferably carried out in the presence of a solvent. Here too, polar solvents are suitable, for instance a halogenated hydrocarbon or an alcohol. Suitable reaction temperatures for this step are in the range of about 0° to about 50° C., preferably between about 10° to about 30° C. The peracid is preferbly used in approximately equivalent amounts or in slightly excess quantities. m-Chloroperbenzoic acid is commercially available and is suitable for use in this reaction. The reaction time is generally 24 hours or longer, for instance up to 48 hours.

Compounds of Formula I are then separated from the reaction mixture, and purified by known purification techniques, such as by elution from a chromatographic column.

The compounds of Formula I can be reacted with a primary or secondary diamine or with a dicarboxylic acid anhydride to form a polymer having a latice structure. Such polymers are useful in the same manner as known micromolecular epoxide resins, e.g. in sealants, adhesives, or as binders in paints. In addition, when the compounds of Formula I are reacted with a polyamine such as ethylenediamine, the resulting reaction products can be used as ion exchangers.

The compounds of Formula I also exhibit cytostatic properties, and are useful in the treatment of various types of cancers, such as several types of leukemia, and against a number of malignant neoplasms, such as cancers of the lungs, cancers of the colon, melanoma, ependymoblastoma, and sarcoma. Also, the compounds of Formula I can be used in combination with known cytostatic agents, or in combination with other techniques useful in the treatment of the above malignancies.

The present invention also relates to pharmaceutical preparations containing a compound of Formula I, and to methods of inhibiting cell growth using the compounds of Formula I.

The compounds of Formula I can be formulated in finished unit dosage forms, e.g. capsules, tablets, sterile solutions for injection such as sterile isotonic solutions, etc., using known pharmaceutical adjuvant materials. Pharmaceutical adjuvant materials for oral dosage forms include, for example, inert diluents, such as calcium carbonate, sodium carbonate, lactose, calcium phosphate or sodium phosphate; granulating and disintegrating agents, for example, maize starch or alginic acid; binding agents, for example, starch, gelatin or acacia; and lubricating agents, for example, magnesium stearate, stearic acid or talc. When tablet form is used, the tablets are preferably enteric coated, to minimize any likelihood that hydrochloric acid in the stomach will affect the glycidyl radicals in the active compounds of the invention.

The finished unit dosage form is formulated to contain from about 1 to about 200 mg. of a compound of Formula I. The actual quantity of active compound chosen within the above range is dependent on the condition to be treated and the dosage frequency desired.

Mammalian patients to be treated with a compound of Formula I are administered a cytostatic (cell growth inhibiting) quantity of the compound of Formula I, either continuously, e.g. by intravenous drip at a rate sufficient to produce a cytostatic effect, or intermittently at convenient intervals using a unit dosage form thereof.

The invention will be better understood from the following examples, which are given for illustration purposes only and are not meant to limit the invention.

EXAMPLE I

PREPARATION OF 1,3-DIGLYCIDYL-LUMAZINE

A mixture consisting of 9.1 g (50 mole) of lumazine hydrate, 92.5 g (1 mole) of epichlorohydrin, 0.2 g of tetramethylammonium bromide, and 20 g of an 8-12 mesh synthetic zeolite molecular sieve, 0.4 nm, was stirred for 3 hours at 90° C., and left standing at room temperature overnight. 4 g (0.1 mole) of powdered sodium hydroxide was then added, stirred for 3 hours at 49° C., and then filtered. The mother liquor was then evaporated, and the residue chromatographed using silica gel (Merck). Methylene chloride containing 4% methanol was used for elution. After the DC control the fractions with the highest $R_f$ value were combined, evaporated, and the residue recrystallized from ethyl acetate. 3.7 g of 1,3-diglycidyl-lumazine were obtained which had a melting point of 145°-147° C.

Epoxide number: calculated: 11.5; found: 10.9.

EXAMPLE II

PREPARATION OF 1,3-DIGLYCIDYL-ALLOXAZINE

The process of EXAMPLE I was carried out using the same conditions and quantities of ingredients, except that the starting material was alloxazine. 3.2 g of 1,3-diglycidyl-alloxazine were obtained, having a melting point of 172°-173° C.

Epoxide number: calculated: 9.8; found: 9.2

EXAMPLE III

Using the isolated products of Examples I and II, the following experiments were performed according to the testing procedures of the National Cancer Institute, Bethesda, Md. 20014, published in "Cancer Chemotherapy Reports", Part 3, September 1972, Vol. 3, No. 2. The above products were prepared immediately prior to application as a 1% aqueous solution for injection. Following the requirements of Protocol 1200 (Page 91c), mice in the number set forth in Protocol were injected with Tumor Type P 388 (leukemia) intraperitoneally at $10^6$ cells/mouse. The mean survival rates of the untreated animals were determined.

In further test groups and according to the above Protocol, the above compounds were injected into the mice. Single doses of 100, 50, 25, and 12.5 mg/kg body weight were administered. In all cases, a significant prolongation of life of the treated test animals, as compared to the average life expectancy of the animals that had not been treated with the active product was achieved. The prolongation rate, T/C, in relation to the dosage of the active compounds was as follows:

| | Retardation of P 388-Tumor: | |
|---|---|---|
| | T/C Value | |
| Applied Dosage mg/kg | EX. I Product | EX. II Product |
| 100 | — | 285 |
| 50 | 250 | 155 |
| 25 | 130 | 156 |
| 12.5 | 120 | 125 |

What is claimed is:

1. A diglycidyl-substituted heterocyclic compound of the formula:

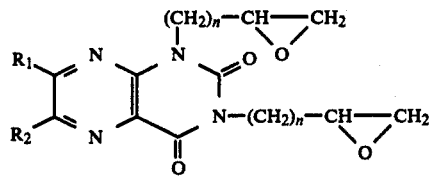

wherein n is the whole number 1 or 2, $R_1$ and $R_2$ are the same or different, and are either hydrogen; or together form a 5- or 6-membered carbocyclic or heterocyclic ring; or are one of the following groups which contain from 1 to 12 carbon atoms:
 (a) a straight or branched chain alkyl group optionally containing from 1 to 3 oxygen or sulfur atoms;
 (b) a straight or branched chain unsaturated hydrocarbon group;
 (c) a cycloaliphatic hydrocarbon group,
 (d) an aromatic hydrocarbon-substituted alkyl group,
 (e) an aromatic hydrocarbon group,
 (f) a heterocyclic group containing at least one heteroatom selected from the group consisting of O, N, P, and S, provided that when the heteroatom is nitrogen, the nitrogen atom is free of hydrogen atoms,
 (g) a cycloaliphatic hydrocarbon-substituted alkyl group, and
 (h) a heterocyclic-substituted alkyl group wherein the heterocyclic moiety contains at least one heteroatom selected from the group consisting of O, N, P, and S, provided that when the heteroatom is nitrogen, the nitrogen atom is free of hydrogen atoms;

and wherein when one or both of the R groups are other than hydrogen, at least one of the following substituents may be present thereon: a straight or branched chain alkyl radical, a straight or branched chain alkenyl radical, a straight or branched chain alkynyl radical, halogen, alkoxy, cyano, alkylmercapto, arylmercapto, alkylsulfoxy, arylsulfoxy, aryloxy, and acyloxy.

2. A compound in accordance with claim 1 wherein the hydrocarbon group in (b) is an alkenyl or alkynyl group, the cycloaliphatic group in (c) and (g) contains a 5- or 6-membered ring, the aromatic hydrocarbon in (d) and (e) is phenyl or naphthyl, and the heterocyclic group in (f) and (h) contains a 5- or 6-membered ring.

3. A compound in accordance with claim 1 wherein when $R_1$ and $R_2$ together form a 5- or 6-membered heterocyclic ring, said ring contains from 1 to 3 heteroatoms selected from the group consisting of O, N, P, and S, provided that when a heteroatom is nitrogen, the nitrogen atom is free of hydrogen atoms.

4. A compound in accordance with claim 1 wherein $R_1$ and $R_2$ together contain not more than 12 carbon atoms.

5. A compound in accordance with claim 1 wherein $R_1$ and $R_2$ together contain not more than 10 carbon atoms.

6. A compound in accordance with claim 1 wherein $R_1$ and $R_2$ together contain not more than 6 carbon atoms.

7. A compound in accordance with claim 1 wherein $R_1$ and $R_2$ together contain not more than 4 carbon atoms.

8. A compound in accordance with claims 1, 2, 4, 5, 6, or 7 wherein the groups which contain from 1 to 12 carbon atoms are straight or branched chain alkyl groups.

9. A compound in accordance with claims 1, 2, 3, 4, 5, 6, or 7 wherein n is 1.

10. A compound in accordance with claim 8 wherein n is 1.

11. A compound in accordance with claim 1 wherein said compound is 1,3-diglycidyl-lumazine.

12. A compound in accordance with claim 1 wherein said compound is 1,3-diglycidyl-alloxazine.

13. A pharmaceutical composition in finished dosage form comprising:

(A) from about 1 to about 200 mg of a substituted heterocyclic compound of the formula:

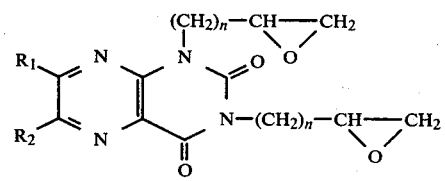

wherein n is the whole number 1 or 2, $R_1$ and $R_2$ are the same or different, and are either hydrogen; or together form a 5- or 6-membered carbocyclic or heterocyclic ring; or are one of the following groups which contain from 1 to 12 carbon atoms:

(a) a straight or branched chain alkyl group optionally containing from 1 to 3 oxygen or sulfur atoms;

(b) a straight or branched chain unsaturated hydrocarbon group, (c) a cycloaliphatic hydrocarbon group, (d) an aromatic hydrocarbon-substituted alkyl group, (e) an aromatic hydrocarbon group, (f) a heterocyclic group containing at least one hetero-atom selected from the group consisting of O, N, P, and S, provided that when the heteroatom is nitrogen, the nitrogen atom is free of hydrogen atoms, (g) a cycloaliphatic hydrocarbon-substituted alkyl group, and (h) a heterocyclic-substituted alkyl group wherein the heterocyclic moiety contains at least one heteroatom selected from the group consisting of O, N, P, and S, provided that when the heteroatom is nitrogen, the nitrogen atom is free of hydrogen atoms;

and wherein when one or both of the R groups are other than hydrogen, at least one of the following substituents may be present thereon: a straight or branched chain alkyl radical, a straight or branched chain alkenyl radical, a straight or branched chain alkynyl radical, halogen, alkoxy, cyano, alkylmercapto, arylmercapto, alkylsulfoxy, arylsulfoxy, aryloxy, and acyloxy; and (B) pharmaceutical adjuvant material.

14. A composition in accordance with claim 13 wherein the hydrocarbon group in (b) is alkenyl or alkynyl group, the cycloaliphatic group in (c) and (g) contains a 5- or 6-membered ring, the aromatic hydrocarbon in (d) and (e) is phenyl or naphthyl, and the heterocyclic group in (f) and (h) contains a 5- or 6-membered ring.

15. A composition in accordance with claim 13 wherein when in said compound $R_1$ and $R_2$ together form a 5- or 6-membered heterocyclic ring, said ring contains from 1 to 3 heteroatoms selected from the group consisting of O, N, P, and S, provided that when a heteroatom is nitrogen, the nitrogen atom is free of hydrogen atoms.

16. A composition in accordance with claim 13 wherein in said compound $R_1$ and $R_2$ together contain not more than 12 carbon atoms.

17. A composition in accordance with claim 13 wherein in said compound $R_1$ and $R_2$ together contain not more than 10 carbon atoms.

18. A composition in accordance with claim 13 wherein in said compound $R_1$ and $R_2$ together contain not more than 6 carbon atoms.

19. A composition in accordance with claim 13 wherein in said compound $R_1$ and $R_2$ together contain not more than 4 carbon atoms.

20. A composition in accordance with claim 13, 14, 15, 16, 17, 18 or 19 wherein in said compound the groups which contain from 1 to 12 carbon atoms are straight or branched chain alkyl groups.

21. A composition in accordance with claim 13, 14, 15, 16, 17, 18 or 19 wherein in said compound n is 1.

22. A composition in accordance with claim 20 wherein in said compound n is 1.

23. A composition in accordance with claim 13 wherein said compound is 1,3-diglycidyl-lumazine.

24. A composition in accordance with claim 13 wherein said compound is 1,3-diglycidyl-alloxazine.

25. A method of inhibiting cell growth in a mammal comprising treating said mammal with a cell growth-inhibiting quantity of a diglycidyl-substituted heterocyclic compound of the formula:

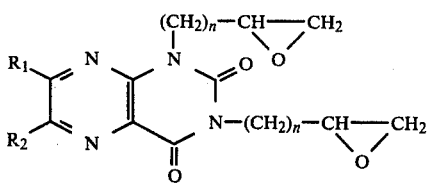

wherein n is the whole number 1 or 2, $R_1$ and $R_2$ are the same or different, and are either hydrogen; or together form a 5- or 6-membered carbocyclic or heterocyclic ring; or are one of the following groups which contain from 1 to 12 carbon atoms:
  (a) a straight or branched chain alkyl group optionally containing from 1 to 3 oxygen or sulfur atoms;
  (b) a straight or branched chain unsaturated hydrocarbon group,
  (c) a cycloaliphatic hydrocarbon group,
  (d) an aromatic hydrocarbon-substituted alkyl group,
  (e) an aromatic hydrocarbon group,
  (f) a heterocyclic group containing at least one heteroatom selected from the group consisting of O, N, P, and S, provided that when the heteroatom is nitrogen, the nitrogen atom is free of hydrogen atoms,
  (g) a cycloaliphatic hydrocarbon-substituted alkyl group, and
  (h) a heterocyclic-substituted alkyl group wherein the heterocyclic moiety contains at least one heteroatom selected from the group consisting of O, N, P, and S, provided that when the heteroatom is nitrogen, the nitrogen atom is free of hydrogen atoms;
and wherein when one or both of the R groups are other than hydrogen, at least one of the following substituents may be present thereon: a straight or branched chain alkyl radical, a straight or branched chain alkenyl radical, a straight or branched chain alkynyl radical, halogen, alkoxy, cyano, alkylmercapto, arylmercapto, alkylsulfoxy, arylsulfoxy, aryloxy, and acyloxy.

26. A process in accordance with claim 25 wherein the hydrocarbon group in (b) is an alkenyl or alkynyl group, the cycloaliphatic group in (c) and (g) contains a 5- or 6-membered ring, the aromatic hydrocarbon in (d) and (e) is phenyl or naphthyl, and the heterocyclic group in (f) and (h) contains a 5- or 6-membered ring.

27. A process in accordance with claim 25 wherein in said compound when $R_1$ and $R_2$ together form a 5- or 6-membered heterocyclic ring, said ring contains from 1 to 3 heteroatoms selected from the group consisting of O, N, P, and S, provided that when a heteroatom is nitrogen, the nitrogen atom is free of hydrogen atoms.

28. A process in accordance with claim 25 wherein in said compound $R_1$ and $R_2$ together contain not more than 12 carbon atoms.

29. A process in accordance with claim 25 wherein in said compound $R_1$ and $R_2$ together contain not more than 10 carbon atoms.

30. A process in accordance with claim 25 wherein in said compound $R_1$ and $R_2$ together contain not more than 6 carbon atoms.

31. A process in accordance with claim 25 wherein in said compound $R_1$ and $R_2$ together contain not more than 4 carbon atoms.

32. A process in accordance with claim 25, 26, 28, 29, 30 or 31 wherein the groups which contain from 1 to 12 carbon atoms are straight or branched chain alkyl groups.

33. A process in accordance with claims 25, 26, 27, 28, 29, 30 or 31 wherein n is 1.

34. A process in accordance with claim 32 wherein n is 1.

35. A process in accordance with claim 25 wherein said compound is 1,3-diglycidyl-lumazine.

36. A process in accordance with claim 25 wherein said compound is 1,3-diglycidyl-alloxazine.

* * * * *